US006531164B1

(12) United States Patent
Credé

(10) Patent No.: US 6,531,164 B1
(45) Date of Patent: Mar. 11, 2003

(54) ENTERAL PHARMACEUTICAL PREPARATION

(75) Inventor: Helfried Hans Rudolf Credé, Somerset West (ZA)

(73) Assignee: The Crede Family Trust, Somerset West (ZA)

( * ) Notice: Subject to any disclaimer, the term of this patent is extended or adjusted under 35 U.S.C. 154(b) by 0 days.

(21) Appl. No.: 09/856,955

(22) PCT Filed: Nov. 29, 1999

(86) PCT No.: PCT/IB99/01900

§ 371 (c)(1),
(2), (4) Date: May 29, 2001

(87) PCT Pub. No.: WO00/32211

PCT Pub. Date: Jun. 8, 2000

(30) Foreign Application Priority Data

Dec. 3, 1998 (ZA) .............................................. 98/11046

(51) Int. Cl.⁷ .............................................. A61K 35/78
(52) U.S. Cl. ........................ 424/764; 424/725; 424/768
(58) Field of Search .................................. 424/764, 725, 424/768

(56) References Cited

U.S. PATENT DOCUMENTS 5,895,652 A  *  4/1999  Giampapa ................ 424/195.1

OTHER PUBLICATIONS

Bashandy, S.A. E. Effect of Nigella sativa oil on Liver and Kidney Functions of Adult and Senile Rats. 1996 Egypt. J. Pharm. Sci., 37(1–6):313–327.*
Gruenwald, J. et al (eds.). PDR for Herbal Medicines. 1998. Medical Economics company, Montvale, N.J., pp. 940–941.*

* cited by examiner

Primary Examiner—Christopher R. Tate
Assistant Examiner—Kailash C. Srivastava

(57) ABSTRACT

An enteral pharmaceutical preparation for the treatment of psoriasis in affected persons includes black cumin oil (nigella sativa). The preparation may further include dietary polyunsaturated fatty acids, such as flax oil (oleum lini).

11 Claims, No Drawings

ENTERAL PHARMACEUTICAL PREPARATION

FIELD OF INVENTION

The present invention relates to an enteral pharmaceutical preparation.

BACKGROUND TO INVENTION

Many people all over the world suffer from the condition known as psoriasis.

The skin of human beings is constantly being renewed. Thereby, as fast as dead cells in the outermost skin layer or epidermis are shed, they are being replaced by cells from the base of the epidermis. Psoriasis takes place when this procedure of replacement becomes "unbalanced", that is when the production of new cells increases while the shedding of dead cells remains normal. This has as consequence that the live cells accumulate and produce sections of inflamed, thickened skin covered by scales. Some persons suffer from extensive affected skin areas, which is unpleasant to view and causes discomfort.

Various creams, ointments, injections and UV light treatments are known for treating psoriasis. However, there is no complete cure for psoriasis and none of the treatments appear to have any lasting effects on the vast majority of sufferers, and many of the remedies cause undesirable side effects.

Even though the condition of psoriasis has been medically identified for more than 100 years, no satisfactory treatment or cure has been found.

Worldwide, more and more people develop psoriatic symptoms, with the highest rate of increase observed in the "developed industrialised" world.

It is an object of the invention to suggest a novel enteral pharmaceutical preparation for treatment of psoriasis, as well as other dermatological disorders.

SUMMARY OF INVENTION

According to the invention, an enteral pharmaceutical preparation is provided for treatment of psoriasis in affected persons, which comprises black cumin oil (nigella sativa) and which further comprises dietary polyunsaturated fatty acids.

The dietary polyunsaturated fatty acids may comprise flax oil (oleum lini).

The black cumin oil (nigella sativa) and the flax oil (oleum lini) may be in a proportion by mass of substantially 1:3.

The black cumin oil (nigella sativa) and the flax oil (oleum lini) may be in a proportion by mass of substantially 1:1.

The preparation may comprise vegetable oils rich in alpha-linolenic (Omega 3) essential fatty acids.

The preparation may comprise vegetable oils rich in alpha-linoleic (Omega 6) essential fatty acids.

The preparation may include essential vitamins and minerals.

The preparation may include the following (in percentage by mass):

| a) Fatty acids: | |
|---|---|
| Omega 3 (Linolenic) | 40.1% |
| Omega 6 (Linoleic) | 29.2% |
| Oleic | 18.8% |
| Palmitic | 6.7% |
| Stearic | 3.3% |
| Myristic | 0.1% |
| Palmitoleic | 0.1% |
| Arachidic | 0.2% |
| Gadoleic | 0.2% |
| Other fatty acids | 0.7% |
| Total fatty acids | 99.4% |
| b) Aromatic Oils: | |
| P-Cymene | 0.25% |
| Thymo-Hydrochinone | 0.21% |
| Alpha-Pinene | 0.09% |
| Other Aromatic Oils | 0.05% |
| Total Aromatic Oils | 0.60% |
| Total Oil Content: | 100.00% |

According to a further aspect of the invention, a method of treating psoriasis in affected persons is provided which comprises the steps of enteral administration of an enteral pharmaceutical preparation including black cumin oil (nigella sativa).

According to yet another aspect of the invention, a method of treating psoriasis in affected persons is provided which comprises the steps of enteral administration of an enteral pharmaceutical preparation including a mixture of black cumin oil (nigella sativa) and flax oil (oleum lini).

The enteral pharmaceutical preparation may further comprise dietary polyunsaturated acids.

The dietary polyunsaturated acids may comprise flax oil (oleum lini).

DESCRIPTION OF PREFERRED EXAMPLES

Example 1

In this example the pharmaceutical preparation in accordance with the invention includes flax oil and black cumin oil. The constitutents of this pharmaceutical preparation are as follows (in percentage by mass):

| Summary: | |
|---|---|
| Total polyunsat. | 75.3% |
| Mono-unsaturates | 16.4% |
| Saturates | 8.3% |
| Total | 100.0% |

In the above the flax oil and Black-Cumin oil respectively are composed as follows:

| Black-Cumin Oil: | |
|---|---|
| a) Fatty Acid Composition: | |
| Myristic | 0.2% |
| Palmitic | 12.4% |
| Palmitoleic | 0.2% |

| | |
|---|---|
| Stearic | 2.7% |
| Oleic | 23.7% |
| Omega 6 (Linoleic) | 57.2% |
| Omega 3 (Linolenic) | 0.2% |
| Arachidic | 0.4% |
| Gadoleic | 0.4% |
| Other | 0.6% |
| Total fatty acids | 98.0% |
| b) Aromatic Oil Composition: | |
| Alpha Terpinene | 0.018% |
| P-Cymene | 0.750% |
| Carvone | 0.008% |
| Thymo-Hydrochinene | 0.618% |
| Alpha-Pinene | 0.272% |
| Beta-Pinene | 0.104% |
| Limonene | 0.070% |
| Others | 0.160% |
| Total Aromatic Oils | 2.0% |
| Flax oil: | |
| Omega 3 (Linolenic) | 60.1% |
| Omega 6 (Linoleic) | 15.2% |
| Oleic | 16.4% |
| Palmitic | 3.9% |
| Stearic | 3.6% |
| Other | 0.8% |
| Total | 100.0% |

From the above it can be seen that the total fatty acids constitute up to 98% of the black-cumin oil, and aromatic oils total 2% by mass respectively.

In one example of treatment, the dosage involved a total of two tablespoons (a total of 20 ml) per day, preferably at breakfast, but in stubborn cases of psoriasis, an initial dose of three to four tablespoons (30 to 40 ml per day) may be required.

The preparation preferably is used as follows:

| | |
|---|---|
| Adults: | 2 tablespoons (20 ml) per day |
| Children: | |
| 3 to 5 years: | 1 teaspoon (5 ml) per day |
| 6 to 10 years: | 2 teaspoons (10 ml) per day |
| 10 to 16 years: | 3 teaspoons (15 ml) per day | with breakfast.

Taste may be a problem and the oil can be mixed into juices or other carrier substances.

It has been found that black-cumin oil may lead to an increased appetite.

Where the oral intake of oils is disliked, it is advised to mix the pharmceutical preparation in accordance with the invention into salads and yoghurt or other suitable carrier dishes.

In the case of patients suffering from diabetes it must be noted that black-cumin oil may lead to low blood sugar (hypoglycaemia), and such a patient's insulin requirements may have to be adjusted accordingly. For this reason diabetes patients have to remain under strict medical supervision until the effects of the pharmaceutical preparation on blood sugar levels have been reliably established.

Example 2

| In this example in summary the following is included (in percentage by mass): | |
|---|---|
| Total poly-unsaturated fatty acids | 69.3% |
| Total mono-unsaturated fatty acids | 18.8% |
| Saturated fatty acids | 11.3% |
| Total aromatic oils | 0.6% |
| Total | 100.0% |

Of the above groupings the compositions are (in percentage by mass):

| a) Fatty acids: | |
|---|---|
| Omega 3 (Linolenic) | 40.1% |
| Omega 6 (Linoleic) | 29.2% |
| Oleic | 18.8% |
| Palmitic | 6.7% |
| Stearic | 3.3% |
| Myristic | 0.1% |
| Palmitoleic | 0.1% |
| Arachidic | 0.2% |
| Gadoleic | 0.2% |
| Other | 0.7% |
| Total fatty acids | 99.4% |
| b) Aromatic Oils: | |
| P-Cymene | 0.25% |
| Thymo-Hydrochinone | 0.21% |
| Alpha-Pinene | 0.09% |
| Other | 0.05% |
| Total aromatic oils | 0.60% |
| Sum Total: | 100.00% |

The other aromatic oils (sum total 0.05%) included:
Carvone, Beta-Pinene, Limonene, Behemic Acid, Sabinene, 1,8-Cinchole, Artemisia-Ketone, Linalool, Beta-Thujone, Bornyl-Acetate, Carvacrole, Thymole, and others.

In traces the following are provided:
Vitamins: B1, B2, B6, Folic Acid, Niacine.
Minerals: Iron, Calcium, Magnesium, Zinc, Selenium
Various Amino Acids and Enzymes.
The preparation preferably is used as follows:
Adults: 2 tablespoons ("large spoon")
children: 3 to 5 years: 1 teaspoon
  6 to 10 years: 2 teaspoons
  10 to 16 years: 3 teaspoons
per day with breakfast.

First improvements are normally noticed after three to four weeks, sometimes sooner, sometimes later. 90% of patients fall within the 3 to 4 weeks category.

The healing process must first commence, after which the "thick skin" will slowly peel off, displaying new pinkish skin areas. The pink colour is due to the fact that new skin must first develop melanin.

The process of healing and regeneration will require several months, varying from individual to individual. Optimum levels of improvement will be reached after approximately 6 months, sometimes sooner, sometimes later.

I claim:
1. An enteral pharmaceutical preparation for treatment of psoriasis in affected persons, which comprises effective amounts of black cumin oil (nigella sativa) and flax oil (oleum lini).

2. A preparation as claimed in claim 1, in which the black cumin oil (nigella sativa) and the flax oil (oleum lini) are in a proportion by mass of about 1:3.

3. A preparation as claimed in claim 1, in which the black cumin oil (nigella sativa) and the flax oil (oleum lini) are in a proportion by mass of about 1:1.

4. A preparation as claimed in claim 1, which further comprises vegetable oils rich in alpha-linolenic Omega 3essential fatty acids.

5. A preparation as claimed in claim 1, which further comprises vegetable oils rich in alpha-linoleic Omega 6essential fatty acids.

6. A preparation as claimed in claim 1, which further comprises essential vitamins and minerals.

7. A preparation as claimed in claim 1, whereby the fatty acid content of the preparation comprises in percentage by mass:

a) Fatty acids:
  Omega 3 Linolenic 40.1%
  Omega 6 Linoleic 29.2%
  Oleic 18.8%
  Palmitic 6.7%
  Stearic 3.3%
  Myristic 0.1%
  Palmitoleic 0.1%
  Arachidic 0.2%
  Gadoleic 0.2%
  Other Fatty acids 0.7%
  Total fatty acids 99.4%,
and wherein the preparation further comprises:
b) Aromatic Oils
  p-Cymene 0.25%
  Thymo-Hydrochinone 0.21%
  Alpha-pinene 0.09%
  Other Aromatic Oils 0.05%
  Total Aromatic Oils 0.60%
    Total Oil Content:
    100.00%.

8. A method of treating psoriasis in affected persons, which comprises the steps of enteral administration to a person in need thereof an enteral pharmaceutical preparation comprising an effective amount of black cumin oil (nigella sativa).

9. A method of treating psoriasis in affected persons, which comprises the steps of enteral administration to a person in need thereof an enteral pharmaceutical preparation comprising an effective amount of a mixture of black cumin oil (nigella sativa) and flax oil (oleum lini).

10. A method as claimed in claim 8, in which the enteral pharmaceutical preparation further comprises dietary polyunsaturated fatty acids.

11. A method as claimed in claim 10, in which the dietary polyunsaturated fatty acids comprise flax oil (oleum lini).

| a) Fatty acids: | |
|---|---|
| Omega 3 Linolenic | 40.1% |
| Omega 6 Linoleic | 29.2% |
| Oleic | 18.8% |
| Palmitic | 6.7% |
| Stearic | 3.3% |
| Myristic | 0.1% |
| Palmitoleic | 0.1% |
| Arachidic | 0.2% |
| Gadoleic | 0.2% |
| Other Fatty acids | 0.7% |
| Total fatty acids | 99.4%, |
| and wherein the preparation further comprises: | |
| b) Aromatic Oils | |
| p-Cymene | 0.25% |
| Thymo-Hydrochinone | 0.21% |
| Alpha-pinene | 0.09% |
| Other Aromatic Oils | 0.05% |
| Total Aromatic Oils | 0.60% |
| Total Oil Content: | 100.00% |

\* \* \* \* \*